(12) United States Patent
Williams et al.

(10) Patent No.: US 8,795,203 B2
(45) Date of Patent: *Aug. 5, 2014

(54) SENSOR CATHETER HAVING REDUCED CROSS-TALK WIRING ARRANGEMENTS

(75) Inventors: Gregory Kent Williams, Sacramento, CA (US); Stephen Charles Davies, Folsom, CA (US); Gerald L. Litzza, Sacramento, CA (US)

(73) Assignee: Volcano Corporation, San Diego, CA (US)

( * ) Notice: Subject to any disclaimer, the term of this patent is extended or adjusted under 35 U.S.C. 154(b) by 161 days.

This patent is subject to a terminal disclaimer.

(21) Appl. No.: 13/431,332

(22) Filed: Mar. 27, 2012

(65) Prior Publication Data

US 2012/0184834 A1 Jul. 19, 2012

Related U.S. Application Data

(63) Continuation of application No. 10/668,451, filed on Sep. 22, 2003, now Pat. No. 8,162,856.

(60) Provisional application No. 60/413,267, filed on Sep. 23, 2002.

(51) Int. Cl.
*A61M 25/00* (2006.01)

(52) U.S. Cl.
USPC .............. 600/585; 600/549; 600/561

(58) Field of Classification Search
CPC .......... A61B 5/06; A61B 5/042; A61B 5/222; A61B 5/083; A61B 19/52
USPC .......... 600/433, 434, 561, 585, 549
See application file for complete search history.

(56) References Cited

U.S. PATENT DOCUMENTS

| | | | |
|---|---|---|---|
| 4,506,500 A | 3/1985 | Miyauchi et al. | |
| 5,374,782 A | 12/1994 | Taylor et al. | |
| 5,591,142 A | 1/1997 | Van Erp | |
| 5,760,341 A * | 6/1998 | Laske et al. | 174/126.2 |
| 5,795,325 A | 8/1998 | Valley et al. | |
| 6,168,570 B1 | 1/2001 | Ferrera | |
| 6,266,551 B1 | 7/2001 | Osadchy et al. | |
| 6,563,107 B2 | 5/2003 | Danisch et al. | |
| 2002/0165448 A1 * | 11/2002 | Ben-Haim et al. | 600/424 |

* cited by examiner

*Primary Examiner* — Max Hindenburg
*Assistant Examiner* — Jonathan M Foreman
(74) *Attorney, Agent, or Firm* — Haynes and Boone, LLP

(57) ABSTRACT

Improved wiring arrangements for sensor catheters are provided to reduce wire-to-wire cross-talk wherein wires connecting the sensor of the sensor catheter to a processing unit are divided into a plurality of wire bundles contained within respective sheaths, with the wires in wire bundle twisted together reduce electromagnetic signal interference among the individual wires, or between wire bundles.

19 Claims, 1 Drawing Sheet

(1)

SENSOR CATHETER HAVING REDUCED CROSS-TALK WIRING ARRANGEMENTS

REFERENCE TO RELATED APPLICATIONS

This application is a continuation of U.S. patent application Ser. No. 10/668,451, filed on Sep. 22, 2003, now U.S. Pat. No. 8,162,856, which claims the benefit of U.S. provisional patent application Ser. No. 60/413,267, filed Sep. 23, 2002, each of which is hereby incorporated by reference in its entirety.

BACKGROUND OF THE INVENTION

This application relates to medical devices such as catheters that have sensors at their distal tips to which electrical wiring is connected.

Sensor catheters are used to gather information during medical procedures for diagnosing and treating patients. Ultrasonic imaging catheters, for example, may be used to gather ultrasonic images of a patient's blood vessels. Alternative imaging techniques also may be used, such as magnetic resonance imaging, optical coherence tomography and infrared imaging. During certain procedures, catheters may be used to gather a variety of physiological parameters such as temperature, pressure, pH, flow velocity and/or volumetric flow. Gradients or changes in physiological parameters across an area of interest may also be determined.

Sensor catheters are typically connected to control and analysis equipment, which may be used to generate images from raw imaging data and display physiological parameters. A number of wires must be run along the length of a typical catheter to connect the control and analysis equipment disposed at the catheter's proximal end to the sensor(s) disposed at the distal catheter tip.

In many instances, there are seven or more wires that convey power supply voltages, ground potential, drive signals, and raw sensor signals to and from the catheter sensors. These wires may be organized as a single cable bundle. However, cross-talk or noise among signal wires is a source of interference when using a sensor catheter to gather sensor measurements. This may adversely affect ringdown performance.

In view of the above, it would be desirable to provide an imaging catheter including improved wiring arrangements to reduce wire-to-wire cross-talk.

SUMMARY OF THE INVENTION

In view of the foregoing, it is an object of the present invention to provide a sensor catheter having improved wiring arrangements for reducing wire-to-wire cross-talk.

In accordance with the principles of the present invention, sensor catheters are provided having improved wiring arrangements that reduce wire-to-wire cross-talk. The wires are grouped in distinct subgroups such as pairs of wires or groups of three or more wires that carry related signals. Accordingly, a group of seven wires may be divided into two twisted wire pairs and one group of three twisted wires. In this manner, wire-to-wire cross-talk is reduced.

By way of example, in an ultrasonic imaging catheter, the two wires that carry sensor signals from the ultrasonic imaging catheter may be grouped together and twisted closely together as a pair. As a result, cross-talk between the two wires is reduced, especially when compared to wire arrangements in which all of the wires are arranged in a single bundle. In addition, wires associated with ultrasonic drive signals also may be grouped together as a pair. Likewise, wires carrying power supply and clock signals (e.g., for use by multiplexer circuits at the catheter's distal end) may be grouped together as a pair.

The above examples are merely illustrative arrangements. According to the present invention, sensor catheters having varying signaling needs and signal wires will require different wire subgroup arrangements. The resulting wire subgroup arrangements may be twisted together to form a single wire group formed of multiple wire subgroups.

Further features of the invention, its nature and various advantages will be more apparent from the accompanying drawings and the following detailed description of the preferred embodiments.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE PREFERRED EMBODIMENTS

Figure 1:
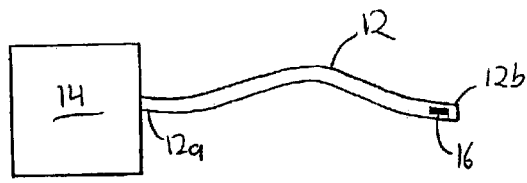
FIG. 1 is a side view of a previously known sensor catheter system.

Referring to FIG. 1, a previously known sensor catheter system 10 comprises catheter 12 including proximal end 12a attached to processing equipment 14 and distal end 12b including sensor assembly 16 comprising one or more sensors. By way of example, sensor assembly 16 may includes a temperature sensor, a pressure sensor, a pH sensor, a flow velocity sensor and/or a volumetric flow sensor for measuring temperature, pressure, pH, flow velocity and flow volume. Of course, sensor assembly 16 may include sensors other than those listed above.

Sensor assembly 16 also may include an imaging sensor, such as an ultrasound, magnetic resonance, optical coherence tomography or infrared imaging sensor. Imaging sensors are typically used to gather images from locations inside a patient's body during surgical and diagnostic procedures. Catheter 12 may be configured to gather images from inside a patient's blood vessels during percutaneous procedures such as cardiological or peripheral intervention. An illustrative catheter that may be used for ultrasound applications is described in commonly assigned U.S. patent application Ser. No. 10/233,870, filed Aug. 29, 2002.

Figure 2:
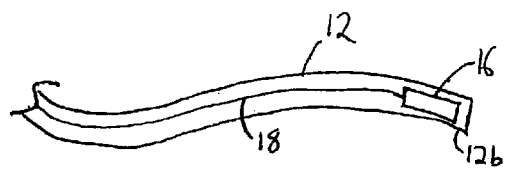
FIG. 2 is a side-sectional view of the previously known sensor catheter of FIG. 1.

Referring to FIG. 2, signals from sensor 16 are transmitted to and from processing equipment 14 via wire bundle 18 including a plurality of wires. Sensor assembly 16 may include an ultrasound sensor that transmits signals to processing equipment 14, which processes the signal data and displays the resulting images on a suitable display screen. Alternatively, sensor assembly 16 may include other sensors that transmit different signals to the processing equipment.

Processing equipment 14 also transmits signals that control the operation of sensor assembly 16. For example, if catheter 12 is an ultrasound imaging catheter, processing equipment 14 transmits drive signals for one or more transducer elements disposed within the sensor assembly. These drive signals cause the transducer elements to emit acoustic vibrations directed towards a target area within the patient's body.

Power supply signals and clock signals (e.g., for synchronizing the timing of circuitry within sensor assembly 16) also may be transmitted to sensor assembly 16 from processing equipment 14 via wire bundle 18. In order to improve overall system performance, it is desirable to reduce cross-talk between the different wires, regardless of the type of signal being transmitted.

Figure 3:
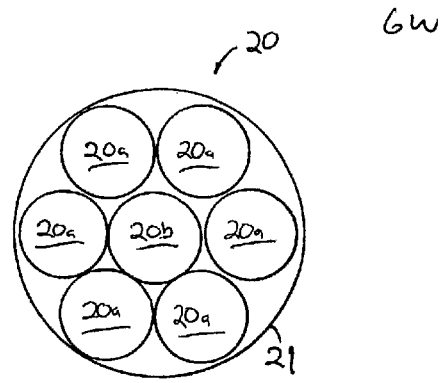
FIG. 3 is a cross-sectional view of a previously known wire bundle for a sensor catheter.

Referring now to FIG. 3, a previously known wiring arrangement 20 for a sensor catheter comprises a single wire bundle having six individual wires 20a radially surrounding central wire 20b. Wiring arrangement further comprises outer sheath 21 for retaining the wires 20a and 20b. This arrangement has the advantage of being relatively compact, but suffers from a relatively high degree of wire-to-wire cross-talk.

Figure 4:
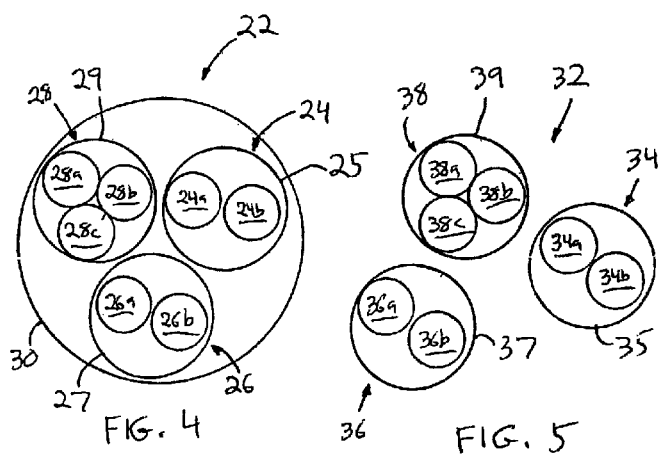
FIG. 4 is cross-sectional view of a first embodiment of a wiring arrangement for a sensor catheter constructed in accordance with the principles of the present invention.

Referring to FIG. 4, a first embodiment of a wiring arrangement for sensor catheter 12 constructed in accordance with the principles of the present invention is described. Wiring arrangement 22 comprises first wire bundle 24 contained within sheath 25, second wire bundle 26 contained within sheath 27 and third wire bundle 28 contained within sheath 29. First wire bundle 24 includes wires 24a and 24b, which are twisted together to assist in electrically isolating the wires from the environment, thereby reducing electromagnetic signal interference among the individual wires. Similarly, second wire bundle 26 includes wires 26a and 26b that are twisted together; third wire bundle 28 includes wires 28a, 28b and 28c that are twisted together. All three wire bundles 24, 26 and 28 are twisted together to form wiring arrangement 22 and housed within outer sheath 30.

Figure 5:
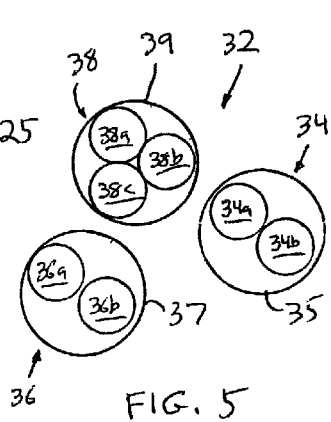
FIG. 5 is cross-sectional view of a second embodiment of a wiring arrangement for a sensor catheter constructed in accordance with the principles of the present invention.

Referring to FIG. 5, a second embodiment of a wiring arrangement for sensor catheter 12 constructed in accordance with the principles of the present invention is described. Wiring arrangement 32 comprises first wire bundle 34 contained within sheath 35, second wire bundle 36 contained within sheath 37 and third wire bundle 38 contained within sheath 39. First wire bundle 34 includes wires 34a and 34b, which are twisted together to assist in electrically isolating the wires from the environment, thereby reducing electromagnetic signal interference among the individual wires. Similarly, second wire bundle 36 includes wires 36a and 36b that are twisted together; third wire bundle 38 includes wires 38a, 38b and 38c that are twisted together. Unlike the embodiment of FIG. 4, wire bundles 34, 36 and 38 of the embodiment of FIG. 5 are not twisted and retained within an outer sheath.

Figure 6:
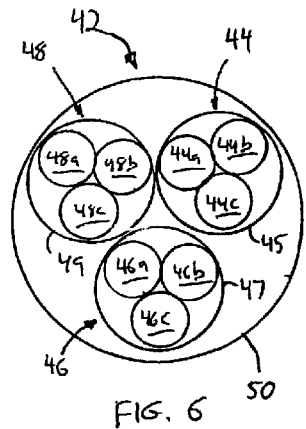
FIG. 6 is cross-sectional view of a third embodiment of a wiring arrangement for a sensor catheter of the present invention.

Referring to FIG. 6, a third embodiment of a wiring arrangement for sensor catheter 12 of the present invention is described. Wiring arrangement 42 comprises first wire bundle 44 contained within sheath 45, second wire bundle 46 contained within sheath 47 and third wire bundle 48 contained within sheath 49. The first pair of wires includes wires 44a, 44b and 44c, which are twisted together to assist in electrically isolating the wires from the environment, thereby reducing electromagnetic signal interference among the individual wires. Similarly, second wire bundle 46 includes wires 46a, 46b and 46c that are twisted together; third wire bundle 48 includes wires 48a, 48b and 48c that are twisted together. All three wire bundles 44, 46 and 48 are twisted together to form wiring arrangement 42 and contained within an outer sheath 50.

Twisting the wires in the wire bundles has been observed to reduce electromagnetic interference among the wires. In some embodiments, the wires are twisted in a clockwise direction, while in others the wires may be twisted in a counter-clockwise direction. Alternatively, wires within different bundles may be twisted in different directions depending upon the application of the sensor catheter. Moreover, multiple wire bundles may be twisted together to form a single wire group. When forming a single wire group from multiple wire bundles, the direction of wire bundle twisting preferably is opposite to the direction in which individual wires are twisted when forming the multiple wire bundles.

The wiring arrangements of FIGS. 4-6 are merely illustrative. As would be appreciated by those of skill in the art, many different wiring arrangements are possible without departing from the scope of the present invention. For example, the wiring arrangement may include 2 or more wire bundles, each wire bundle including two or more individual wires.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. A method, comprising:
    providing a catheter having proximal portion and a distal portion;
    coupling a sensor assembly to the distal portion of the catheter; and
    coupling a plurality of wires to the sensor assembly such that the plurality of wires extend from the distal portion of the catheter to the proximal portion of the catheter, wherein the plurality of wires are divided into at least first and second wire bundles, each of the wires in at least the first and second wire bundles twisted together such that the wires in at least the first and second wire bundles are not arranged side by side in order to reduce electromagnetic interference between the wires, wherein the plurality of wires carry control signals transmitted to the sensor assembly and sensor signals transmitted from the sensor assembly, and wherein at least the first and second wire bundles are twisted together and disposed within an outer sheath having an inner wall forming a space containing at least the first and second wire bundles of the plurality of wires;
        wherein the first wire bundle of the plurality of wires coupled to the sensor assembly consists of a pair of wires;
        wherein the second wire bundle consists of a pair of wires;
        wherein the plurality of wires coupled to the sensor assembly are further divided into a third wire bundle, wherein the wires in the third wire bundle are twisted together to reduce electromagnetic interference;
        wherein the third wire bundle consists of three wires.

2. A method, comprising:
    providing a catheter having proximal portion and a distal portion;
    coupling a sensor assembly to the distal portion of the catheter; and
    coupling a plurality of wires to the sensor assembly such that the plurality of wires extend from the distal portion of the catheter to the proximal portion of the catheter, wherein the plurality of wires are divided into at least first and second wire bundles, each of the wires in at least the first and second wire bundles twisted together such that the wires in at least the first and second wire bundles are not arranged side by side in order to reduce electromagnetic interference between the wires, wherein the plurality of wires carry control signals transmitted to the sensor assembly and sensor signals transmitted from the sensor assembly, and wherein at least the first and second wire bundles are twisted together and disposed within an outer sheath having an inner wall forming a space containing at least the first and second wire bundles of the plurality of wires;

wherein the wires in the first wire bundle are twisted together in a first direction and the wires in the second wire bundle are twisted together in a second direction substantially opposite the first direction.

3. The method of claim 2, wherein the first wire bundle of the plurality of wires coupled to the sensor assembly consists of a pair of wires.

4. The method of claim 3, wherein the pair of wires of the first wire bundle is twisted together in a clockwise direction.

5. The method of claim 3, wherein the pair of wires of the first wire bundle is twisted together in a counter-clockwise direction.

6. The method of claim 3, wherein the second wire bundle consists of a pair of wires.

7. The method of claim 6, wherein the plurality of wires coupled to the sensor assembly are further divided into a third wire bundle, wherein the wires in the third wire bundle are twisted together to reduce electromagnetic interference.

8. The method of claim 7, wherein the first, second, and third wire bundles are twisted together and disposed within the outer sheath.

9. A method, comprising:
providing a catheter having proximal portion and a distal portion;
coupling a sensor assembly to the distal portion of the catheter; and
coupling a plurality of wires to the sensor assembly such that the plurality of wires extend from the distal portion of the catheter to the proximal portion of the catheter, wherein the plurality of wires are divided into at least first and second wire bundles, each of the wires in at least the first and second wire bundles twisted together such that the wires in at least the first and second wire bundles are not arranged side by side in order to reduce electromagnetic interference between the wires, wherein the plurality of wires carry control signals transmitted to the sensor assembly and sensor signals transmitted from the sensor assembly, and wherein at least the first and second wire bundles are twisted together and disposed within an outer sheath having an inner wall forming a space containing at least the first and second wire bundles of the plurality of wires;

wherein the wires in the first wire bundle are twisted together in a first direction, the wires in the second wire bundle are twisted together in the first direction, and the first and second wire bundles are twisted together in a second direction substantially opposite the first direction.

10. A method, comprising:
providing a flexible elongate member having a proximal portion and a distal portion;
disposing a sensor assembly adjacent the distal portion of the flexible elongate member; and
coupling a plurality of wires to the sensor assembly such that the plurality of wires extend from the sensor assembly to a connector adjacent the proximal portion of the flexible elongate member, the plurality of wires configured to carry control signals to the sensor assembly and sensor signals from the sensor assembly, wherein the plurality of wires are divided into a first wire bundle and a second wire bundle, each of the wires in the first and second wire bundles twisted together such that the wires are not arranged side by side in order to reduce electromagnetic interference between wires in the first and second wire bundles, wherein the wires of the first wire bundle are disposed within a first sheath, wherein the wires of the second wire bundle are disposed within a second sheath, and wherein the first and second sheaths are twisted together and disposed within an outer sheath having an inner wall forming a space containing the first and second wire bundles.

11. The method of claim 10, wherein the wires in the first wire bundle are twisted together in a clockwise direction.

12. The method of claim 11, wherein the wires in the second wire bundles are twisted together in a counter-clockwise direction.

13. The method of claim 10, wherein at least one of the first and second wire bundles consists of a pair of wires.

14. The method of claim 10, wherein the plurality of wires further are divided into a third wire bundle, wherein the wires in the third wire bundle are twisted together.

15. The method of claim 14, wherein the third wire bundle consists of three wires.

16. The method of claim 14, wherein the first, second, and third wire bundles are twisted together and disposed within the outer sheath.

17. The method of claim 10, wherein the wires in the first wire are twisted together in a first direction, the wires in the second wire bundle are twisted together in the first direction, and the first and second wire bundles are twisted together in a second direction substantially opposite the first direction.

18. The method of claim 10, wherein the sensor assembly includes at least one of an imaging sensor, a temperature sensor, a pressure sensor, a pH sensor, a flow velocity sensor, and a volumetric flow sensor.

19. The method of claim 18, wherein the sensor assembly includes an imaging sensor selected from the group of imaging sensors consisting of an ultrasound imaging sensor, a magnetic resonance imaging sensor, an optical coherence tomography imaging sensor, and an infrared imaging sensor.

\* \* \* \* \*